(12) United States Patent
Park et al.

(10) Patent No.: US 6,391,625 B1
(45) Date of Patent: May 21, 2002

(54) BIOCHIP AND METHOD FOR PATTERNING AND MEASURING BIOMATERIAL OF THE SAME

(75) Inventors: Je Kyun Park; Tae Han Kim, both of Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 09/604,405

(22) Filed: Jun. 27, 2000

(30) Foreign Application Priority Data

Jun. 28, 1999 (KR) .............................. 99-24967

(51) Int. Cl.[7] .................. C12M 1/34; G01N 33/53; C07H 21/00; C07H 21/04; G11B 7/24
(52) U.S. Cl. .................. 435/287.2; 435/6; 435/7.2; 435/91.1; 435/91.2; 536/221; 536/23.1; 536/24.3; 536/24.31; 536/24.32; 536/24.33; 369/275.1; 369/275.3; 369/275.4
(58) Field of Search .................. 435/5, 6, 7.2, 91.1, 435/91.2, 287.2; 536/22.1, 23.1, 24.3, 24.31, 24.32, 24.33; 369/275.1, 275.3

(56) References Cited

U.S. PATENT DOCUMENTS

| | | | |
|---|---|---|---|
| 5,091,652 A | | 2/1992 | Mathies et al. .......... 250/458.1 |
| 5,143,854 A | | 9/1992 | Pirrung et al. .............. 436/518 |
| 5,474,796 A | | 12/1995 | Brennan ..................... 427/2.13 |
| 5,885,837 A | * | 3/1999 | Winkler et al. ............. 435/91.1 |
| 6,060,237 A | * | 5/2000 | Nygren et al. ................. 435/6 |
| 6,156,501 A | * | 12/2000 | McGall et al. ................. 435/6 |
| 6,212,158 B1 | * | 4/2001 | Ha et al. ................. 369/275.4 |

FOREIGN PATENT DOCUMENTS

JP 09254809 * 4/1999

OTHER PUBLICATIONS

Schena et al., (1998) "Microarrays: biotechnology's discovery platform for functional genomics" TIBTECH, vol. 16: 301–306.

* cited by examiner

*Primary Examiner*—Jeffrey Siew
(74) *Attorney, Agent, or Firm*—Morgan, Lewis & Bockius LLP (57) ABSTRACT

A biochip including a DNA chip and a protein chip and a method for patterning and measuring biomaterial of the same are disclosed. The method for patterning a biomaterial of the biochip including a reflecting layer and an active layer on a substrate includes the steps of: rotating the biochip; successively irradiating pulse type laser beams to the rotating biochip to activate predetermined regions of the active layer; and fixing a biomaterial pattern on the activated predetermined regions. A method for measuring the patterned biomaterial includes the steps of: reacting a biomaterial labeled with at least one dye material with the biochip; rotating the biochip reacted with at least one biomaterial; successively irradiating laser beams to the rotating biochip; and detecting and processing light derived from the biochip as a result of reaction of the biomaterial to measure the biomaterial. Thus, the biochip having reliability and high packing density can be fabricated at low cost and the biomaterial of the biochip can be measured at high speed without using expensive equipments.

19 Claims, 12 Drawing Sheets

FIGF.6b

BIOCHIP AND METHOD FOR PATTERNING AND MEASURING BIOMATERIAL OF THE SAME

BACKGROUND OF THE INVENTION

1. Field of the Invention

The present invention relates to a biochip, and more particularly, to a biochip including a DNA chip and a protein chip and a method for patterning and measuring biomaterial of the same.

2. Discussion of the Related Art

Generally, a biochip is a hybrid device made of an existing semiconductor chip type by combining bio-organic matters isolated from creatures, such as enzymes, proteins, antibodies, DNA, microbes, animal and plant cells, animal and plant organs and neurons, with inorganic matters such as semiconductors.

The biochip acts to diagnose infectious diseases or analyze genes by using inherent functions of biomolecules and mimicking functions of organisms. The biochip acts as a new function device for processing new information.

It is expected that the biochip will be a core device of a biocomputer which thinks like an organism and responds to external action, because the biochip has characteristics such as high packing density, realization of functions at molecular level, and parallel processing function together with potentials which surpass functions of the existing semiconductor.

According to used biomaterials and systemization, the biochip can be classified into a DNA chip integrated with DNA probes, a protein chip with proteins such as enzymes, antibodies/antigens, and bacteriorhodopsins, and a neuron chip with neurons. Also, in a broad definition, the biochip includes a lab chip having automatic analysis functions including pretreatment of samples, biochemical reaction, detection, and data analysis, and a biosensor having detection and analysis functions of various biochemical materials.

To develop such a biochip, it is necessary to efficiently realize molecular interface between biomaterial and semi-conductor such as silicon, thereby optimizing inherent functions of the biomaterials.

Particularly, to produce a biochip such as a DNA chip and a protein chip, it is important that biomaterials are high integrated in a limited area of micrometer scale. The reason why is that highly integrated DNA chip has an improved decoding ability of gene information.

Presently, a DNA chip having 400,000 probes therein can be fabricated.

Although conventional methods for fabricating a DNA chip are different from each other, there are similarities in that DNA samples are hybridized with DNA probes on a surface such as silicon or glass substrate and then hybridization results are compared with known DNA base sequences. The hybridization means that a single-stranded DNA molecule called a probe (base sequence which can hybridize specifically with complementary base sequence) is fixed on a solid, so as to form a double-stranded DNA together with a gene site having complementary base sequences on a target solution.

Accordingly, the conventional methods are similar in that fixed DNA, target DNA or double-stranded DNA is labeled to obtain desired information.

The DNA chip has several advantages. First, it is not necessary to perform complicate steps such as gel electrophoresis and filter hybridization. Second, since a probe having a short length of about 15~30 bases is used, a result of hybridization can be confirmed within relatively short time. Third, if a DNA chip having all possible base sequences is fabricated, hybridization patterns are simply compared to confirm the presence of hereditary disease.

However, several problems still remain in the current DNA chip technology in the following aspects. That is, a DNA array of high density should be fabricated at low cost, hybridization reaction should be optimized, and detection method and pattern comparison method should be improved.

The DNA chip can be fabricated by two methods. That is, the DNA chip can be fabricated in such a manner that synthesized oligonucleotides or peptide nucleic acid (PNA) is laid on a chip. Alternatively, the DNA chip can be fabricated in such a manner that a probe is formed by directly synthesizing oligonucleotides on a chip. These two methods have been utilized most actively in the United States of America, and many results and actual fabrication technologies are being commercially used.

Of the fabrication technologies, there is a method that polypeptides are synthesized in situ on a silicon substrate using photolithography method mainly used in the semiconductor process (U.S. Pat. No. 5,143,854).

However, the fabrication of a DNA chip requires decades of masks which have their own pattern. That is to say, in case where an oligonucleotide probe having a length of 25 bases, four masks are required to form one base layer and total 100 masks are required. Since the fabrication process requires about 100 cycles, complicate process steps and expensive cost are caused in case of mass production of a DNA chip. Furthermore, washing and mask aligning processes are required in each process, and expensive equipment is required.

In other words, since the costs of DNA chip design and oligonucleotide synthesis are expensive, a small quantity of production with various kinds is impossible due to problems related to the required time and costs from order to production.

Besides the above method, there is another method for forming oligonucleotide on a surface of a chip by electrically discharging any one of four bases using piezoelectric printing method of ink jet printer (U.S. Pat. No. 5,474,796).

However, although oligonucleotide of 40~50 bases can be formed, integration is limited by aligning process and pattern size of about 100 $\mu$m. Also, spread occurs when injecting samples and operating a spraying device.

Furthermore, there are a micropipetting method and a spotting method of cDNA (TIBTECH 16; 301~306, 1998).

These methods have problems that a DNA chip cannot be fabricated at high density and mass production is limited. Thus, these methods are applicable to fabrication of a DNA chip for study.

Meanwhile, the DNA chip and the DNA microarray have different fabrication methods but are similar in that different oligonucleotides are aligned on a square spot having a certain size in a check pattern.

Accordingly, to measure a fluorescent material used to confirm hybridization reaction, expensive image scanner is required (U.S. Pat. No. 5,091,652).

In other words, this method has problems that a system having a bidirectional linear translator is required to detect samples, software for processing image data of large capacity is required, and image scan time is long.

The related art biochip has the following disadvantages.

First, when a biochip is fabricated, the process steps are complicate, and a number of masks and expensive equipment are required, thereby preventing mass production.

Second, since the process has limitation in minimizing the size of a pattern material, the biochip of high density cannot be fabricated.

Third, to measure a pattern material of the biochip, expensive equipments and relatively long time are required.

SUMMARY OF THE INVENTION

Accordingly, the present invention is directed to a biochip and a method for patterning and measuring biomaterial of the same, that substantially obviate one or more of the problems due to limitations and disadvantages of the related art.

An object of the present invention is to provide a biochip having reliability and high packing density at low cost and a method for patterning and measuring biomaterial of the same.

Additional features and advantages of the invention will be set forth in the description which follows, and in part will be apparent from the description, or may be learned by practice of the invention. The objectives and other advantages of the invention will be realized and attained by the scheme particularly pointed out in the written description and claims hereof as well as the appended drawings.

To achieve these and other advantages and in accordance with the purpose of the present invention, as embodied and broadly described, a biochip according to the present invention includes a substrate, a reflecting layer formed on an entire surface of the substrate, an active layer formed on the reflecting layer, and a biomaterial pattern formed on a predetermined region of the active layer, wherein the substrate has a round shape, and the substrate includes a groove region and a land region. A boundary between the groove region and the land region of the substrate are formed in a wobble form. Furthermore, the substrate is formed of any one of glass, polycarbonate, polytetrafluorethylene, polystyrene, silicon oxide, and silicon nitride, the reflecting layer is formed of gold or aluminum, and the active layer is formed of a silicon oxide film formed on the reflecting layer, and a reaction material and a photosensitive material sequentially formed on the silicon oxide film.

In another aspect, a method for patterning a biomaterial in the above biochip includes the steps of rotating the biochip, irradiating a pulse type laser beam to the rotating biochip to successively activate predetermined regions of the active layer, fixing a biomaterial pattern on the activated predetermined regions, and sequentially repeating the above steps.

The laser beam is irradiated to the biochip while moving from a central portion of the biochip to its outer circumference, or from the outer circumference to the central portion in a straight line. The laser beam is classified into a first beam for sensing a track of the biochip to transmit a position signal for activation and a second beam for activating a spot of the biochip in accordance with the position signal of the first beam.

In other aspect, a method for measuring a biomaterial including a reflecting layer and an active layer on a substrate, includes the steps of: reacting a biomaterial labeled with at least one dye material with the biochip; rotating the biochip reacted with at least one biomaterial; successively irradiating laser beams to the rotating biochip; and detecting and processing light derived from the biochip as a result of reaction of the biomaterial to measure the biomaterial, wherein the laser beams have different wavelengths in accordance with the dye material labeled in the biomaterial, and the dye material is formed of fluorescent material or infrared dye material.

It is to be understood that both the foregoing general description and the following detailed description are exemplary and explanatory and are intended to provide further explanation of the invention as claimed.

BRIEF DESCRIPTION OF THE DRAWINGS

The invention will be described in detail with reference to the following drawings in which like reference numerals refer to like elements wherein:

FIGS. 6a and 6b show position of laser beams and their movement direction during patterning process;

DETAILED DESCRIPTION OF THE PREFERRED EMBODIMENTS

Reference will now be made in detail to the preferred embodiments of the present invention, examples of which are illustrated in the accompanying drawings.

A process for fabricating a round plate type biochip and a structure of the biochip will be described with reference to the accompanying drawings.

The biochip of the present invention is fabricated by three processes.

The first process is mastering process for making a mold called a stamper. The second process is injection molding capable of fabricating biochips in large quantities by injection, compression, or photo-polimerization(2P) using the stamper. The third is patterning process of a biomaterial by coating a reflecting film, an oxide film and a reaction material with the biomaterial.

Figure 1A:
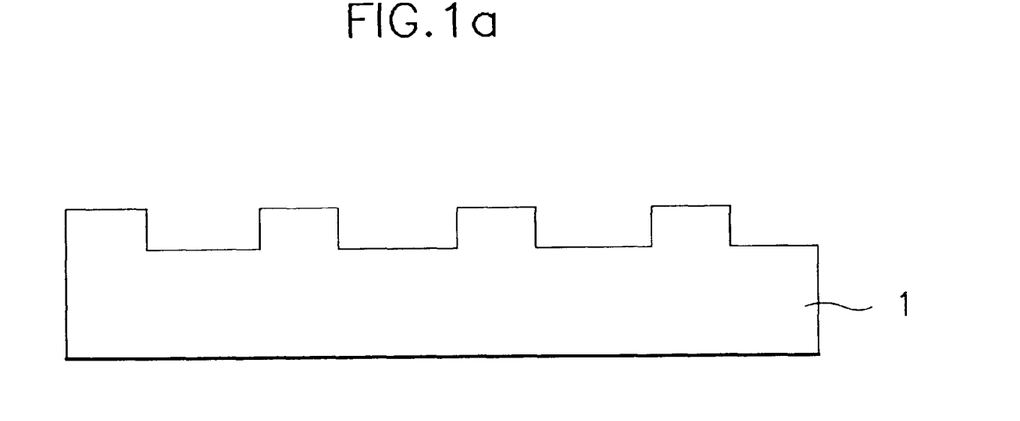
FIGS. 1a to 1c show a fabrication process of a biochip according to the present invention.

As shown in FIG. 1a, a substrate 1 having a land region and a groove region is fabricated by mastering and injection molding processes. The substrate 1 is formed of an inorganic material such as glass, polycarbonate, polytetrafluorethylene, polystyrene, silicon oxide, and silicon nitride.

Figure 2A:
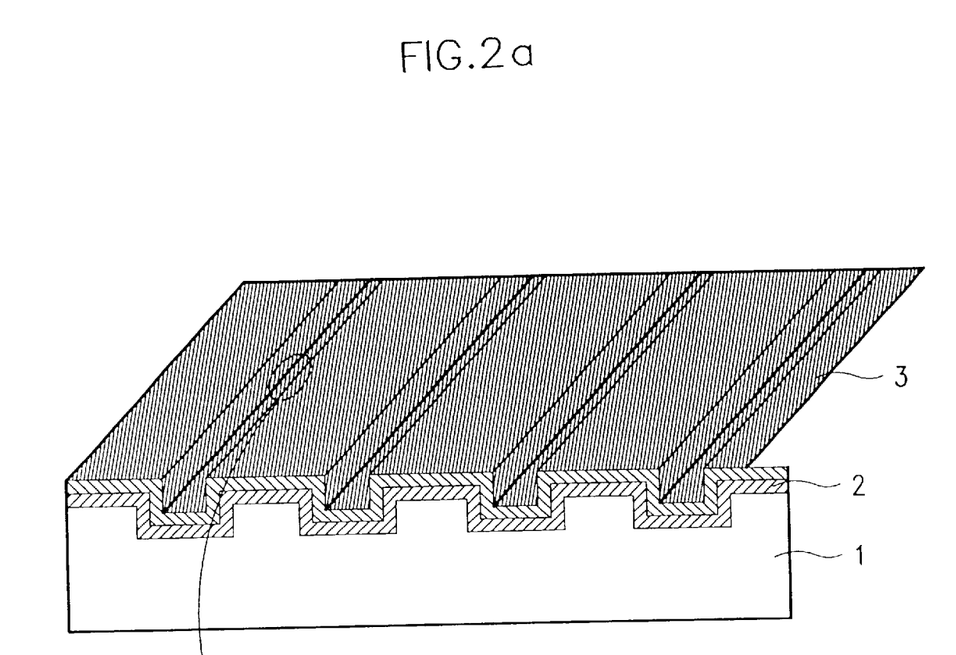
FIG. 2 shows a wobble track of a biochip according to the present invention.
Figure 2B:
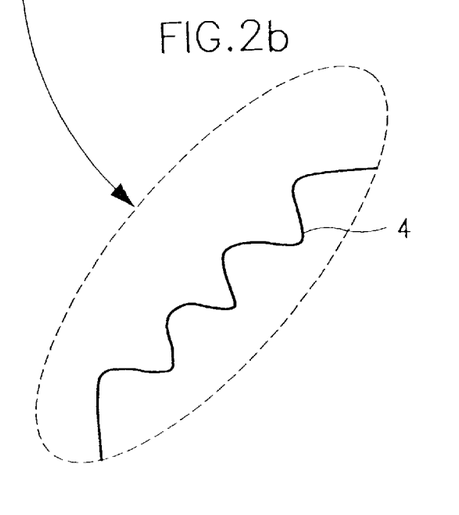

The boundary between the land region and the groove region is of a wobble form 4 as shown in FIG. 2. This is the reason why that a desired position sector is to be accurately searched when patterning or measuring a biomaterial.

Figure 1B:
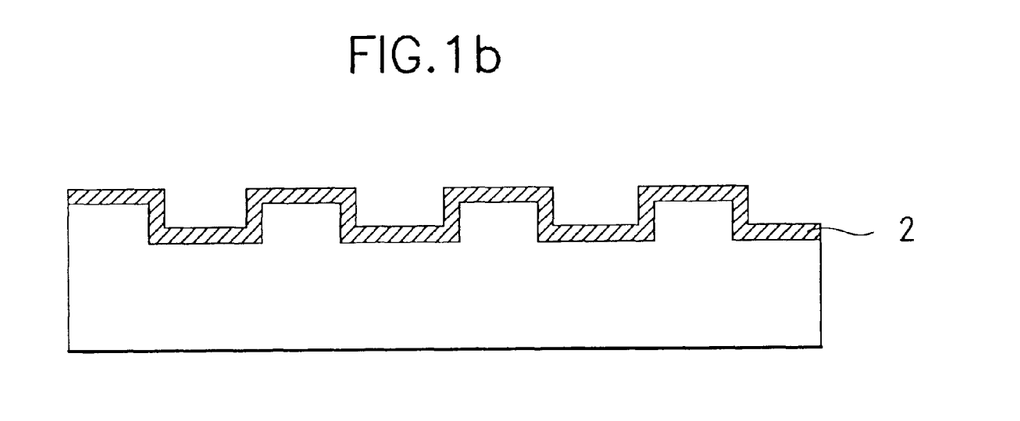
Figure 1C:
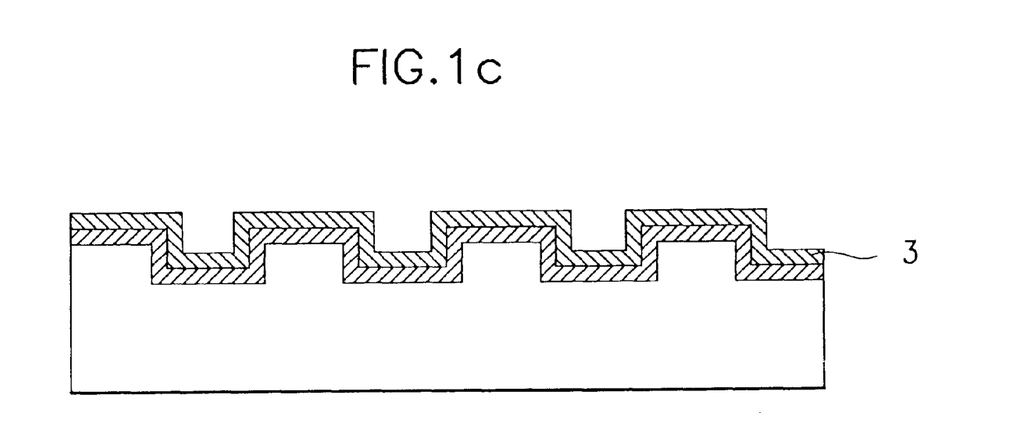

Subsequently, as shown in FIG. 1b, a metal reflecting layer 2 such as Au or Al is coated on an entire surface of the substrate 1. Finally, as shown in FIG. 1c, a silicon oxide film 3 is coated by sputtering to induce a reaction group with the biomaterial.

Figure 3:
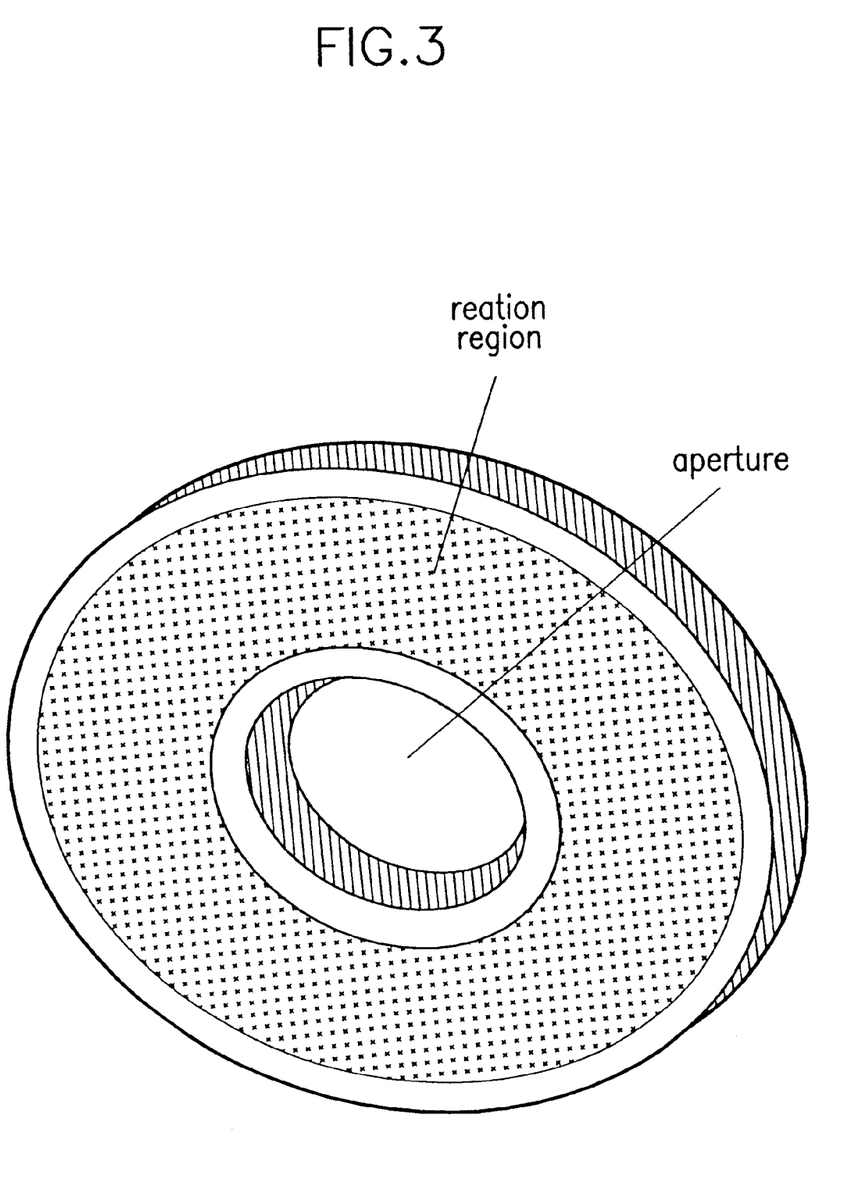
FIG. 3 is a perspective view showing a structure of a round plate type biochip according to the present invention.

The finished round plate type biochip substrate has a shape similar to an existing compact disc, as shown in FIG. 3. The round plate type biochip substrate has a thickness of 1.2 mm, and a diameter of 1 cm, 2 cm, 4 cm, 8 cm or 12 cm.

A method for patterning a biomaterial in the aforementioned biochip will be described with reference to FIGS. 4a to 4k.

Figure 4A:
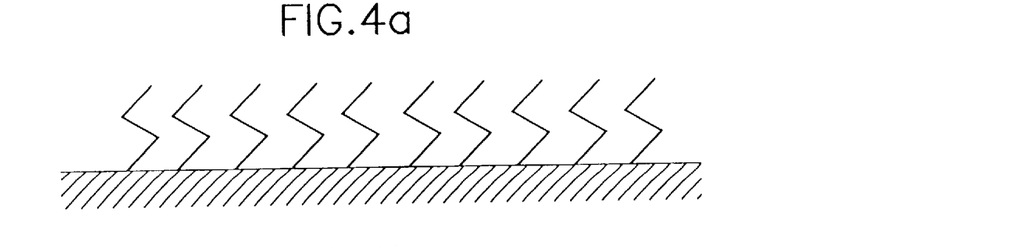
FIGS. 4a to 4k and 5a to 5l show the process for patterning a biomaterial of a biochip according to the present invention.
Figure 4B:
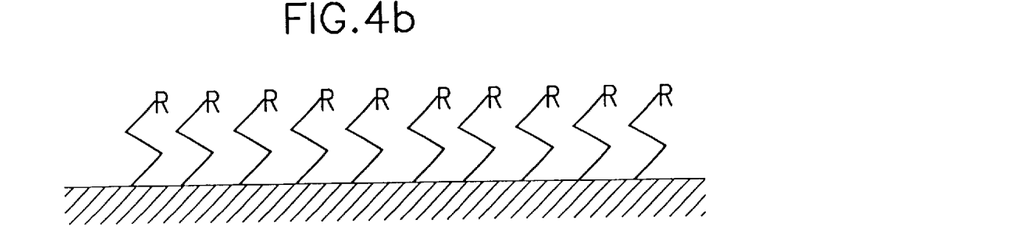

As shown in FIG. 4a, a surface of the silicon oxide film formed along a tract on the round plate type biochip substrate is silanizated using a silane based material such as X—Si(OCH$_3$)$_3$ and X—SiCl$_3$, where X is a function group. Then, a reaction group such as —NH$_3$, is formed using glutaraldehyde. Subsequently, as shown in FIG. 4b, a photosensitive material R is coated on the reaction group.

The silanization and coating of the photosensitive material may be performed in a vessel containing a reaction solution or by spin coating. At this time, the resultant reaction byproducts are removed by cleaning and washing.

Figure 4C:
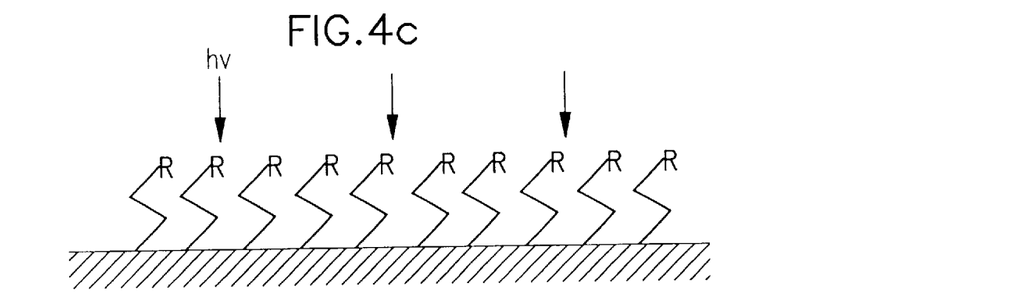

As shown in FIG. 4c, the substrate coated with the photosensitive material is rotated and pulse type laser beams are irradiated to the rotating substrate to successively activate regions where the biomaterial will be formed.

Figure 6A:
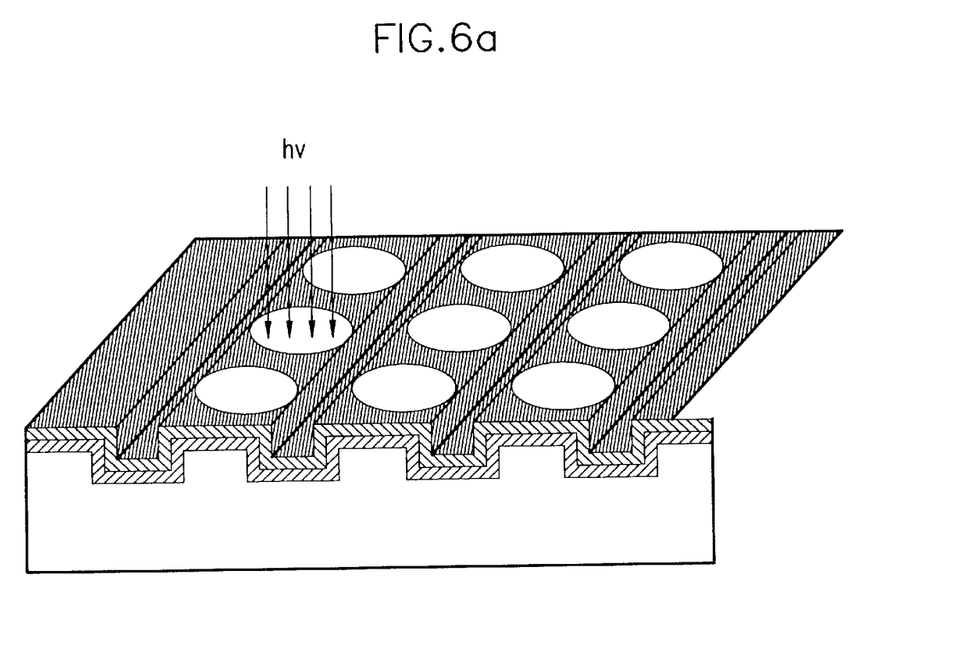

In other words, as shown in FIG. 6a, the laser beams emitted from a laser diode reads a wobble track formed along a track of the substrate to search a desired position in accordance with a computer program so that the photosensitive material on the track is activated. At this time, a spot of the laser beams has a diameter of about 1~100 $\mu$m and is adjustable to be suitable for high integration of a biomaterial pattern.

Meanwhile, an optical pick-up device for emitting laser beams successively irradiates the laser beams while moving from a central portion of the substrate to its outer circumference, or from the outer circumference to the central portion in a straight line. Accordingly, the optical pick-up device has a higher patterning speed than the related art and thus is suitable for mass production.

To improve reliability, the optical pick-up device may include a first light source for sensing the track of the biochip to transmit a position signal for activation and a second light source for activating a spot of the substrate in accordance with the position signal of the first light source.

Figure 4D:
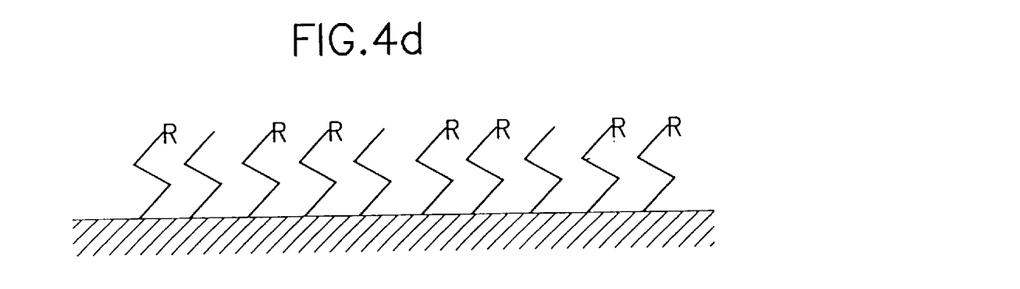

Thus, in a state that the substrate is rotating at a certain speed, the optical pick-up device irradiates pulse type laser beams so that an active pattern is formed to fix the biomaterial on a spot of the substrate as shown in FIG. 4d.

Figure 4E:
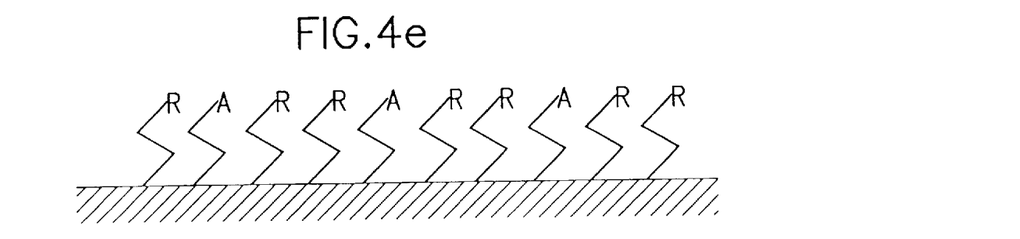
Figure 4F:
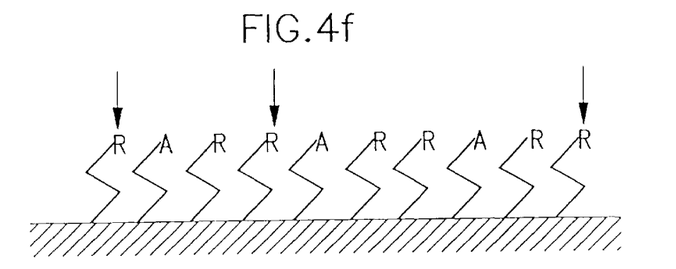
Figure 4G:
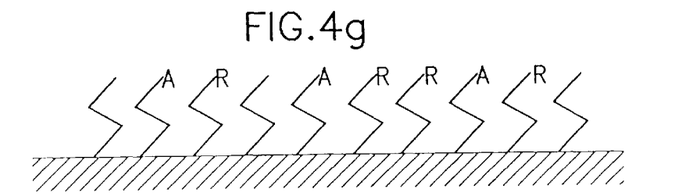
Figure 4H:
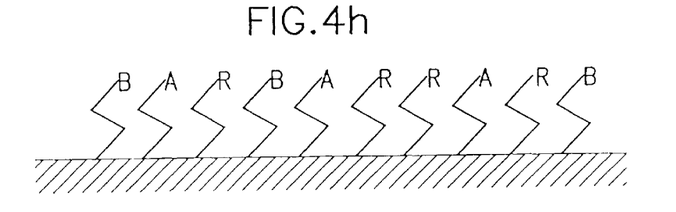
Figure 4I:
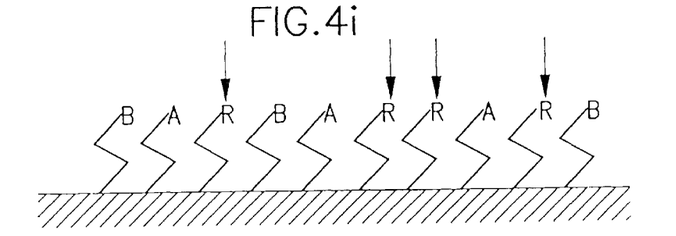
Figure 4J:
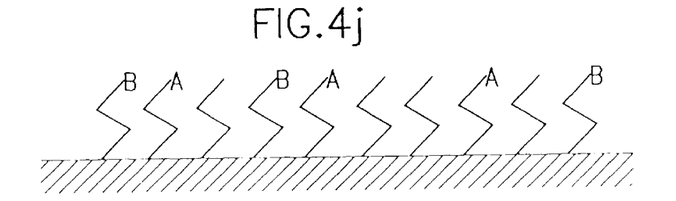
Figure 4K:
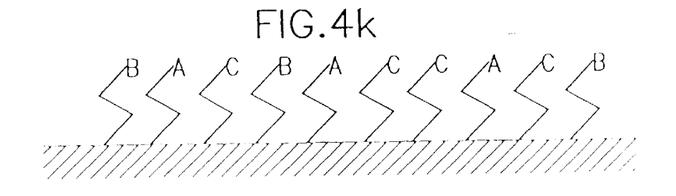
Figure 5A:
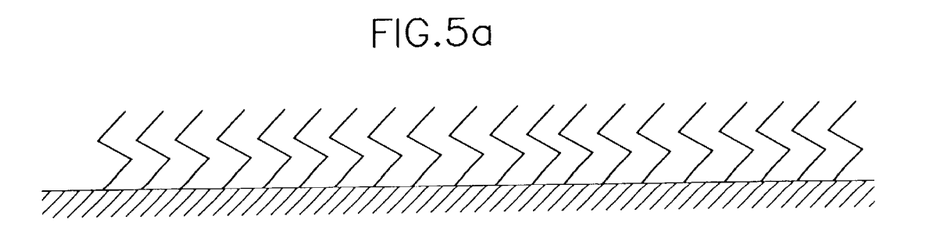
Figure 5B:
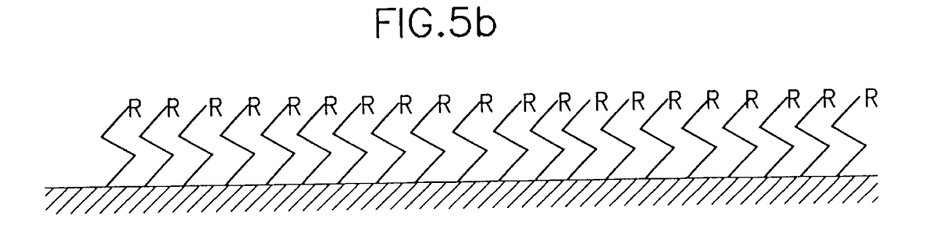
Figure 5C:
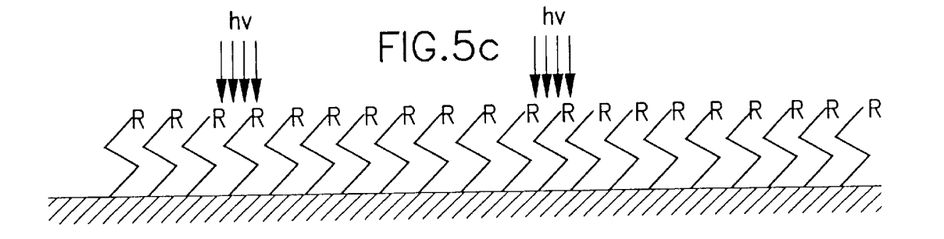
Figure 5D:
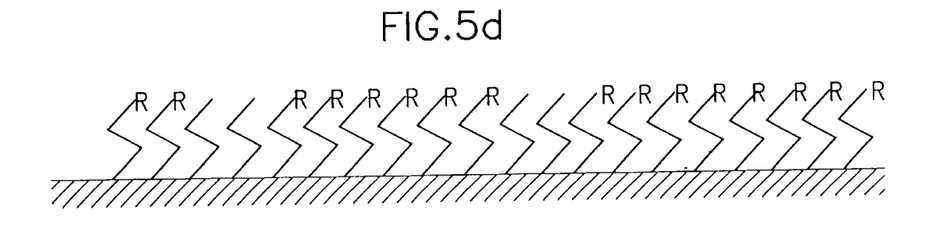
Figure 5E:
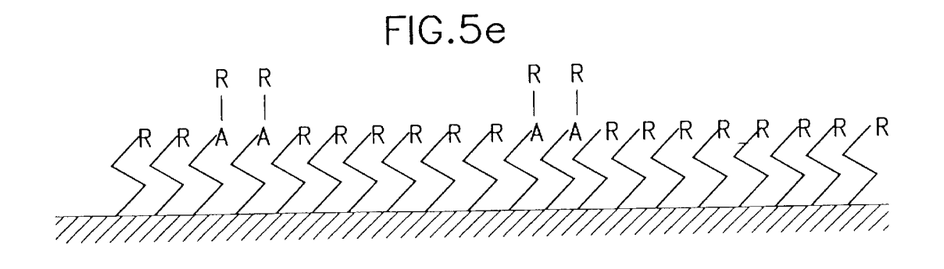
Figure 5F:
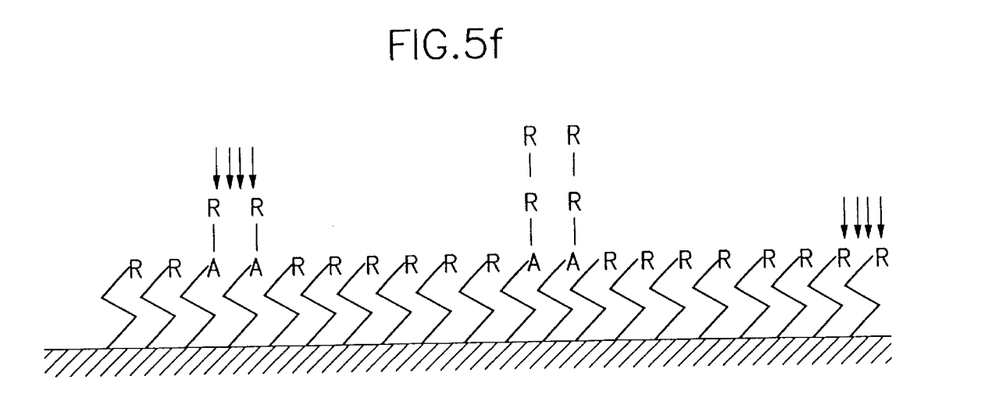
Figure 5G:
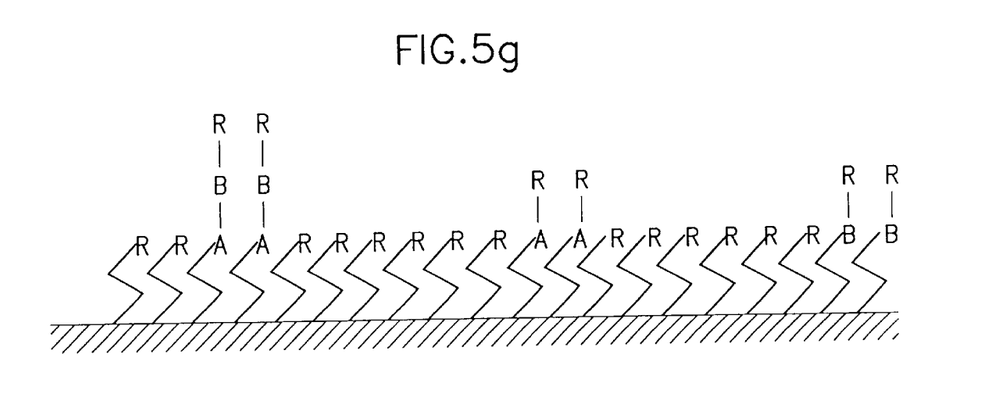
Figure 5H:
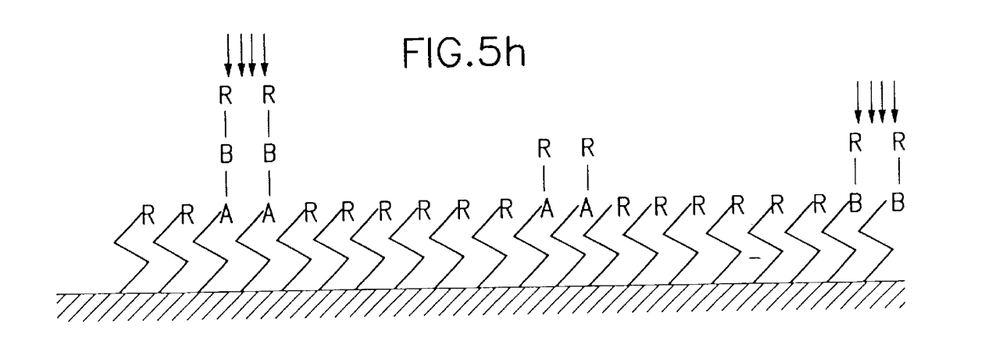
Figure 5I:
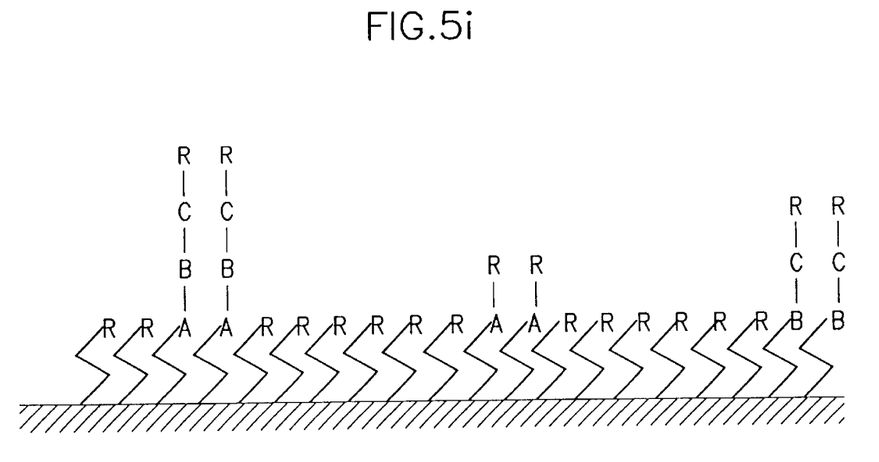
Figure 5J:
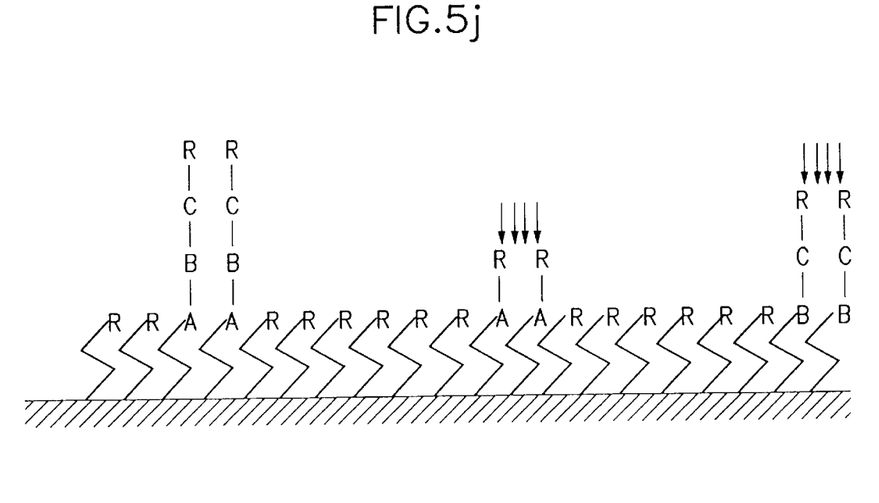
Figure 5K:
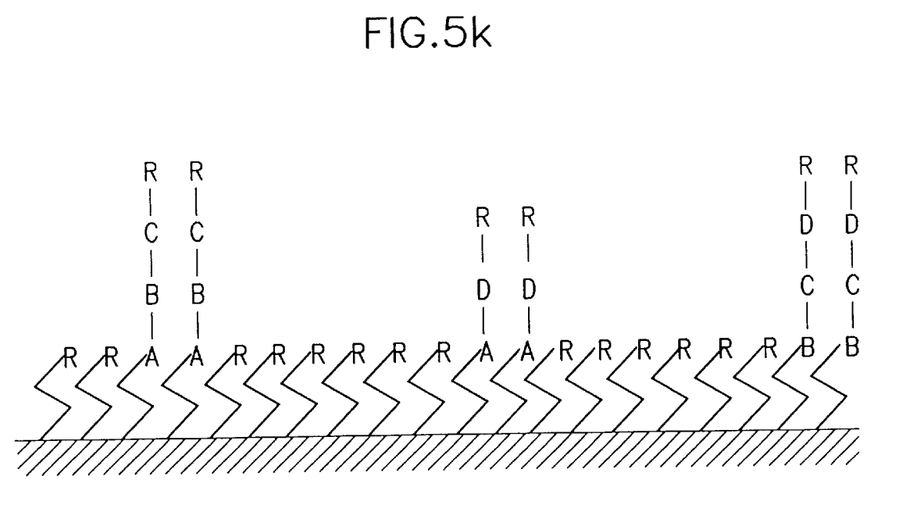
Figure 5L:
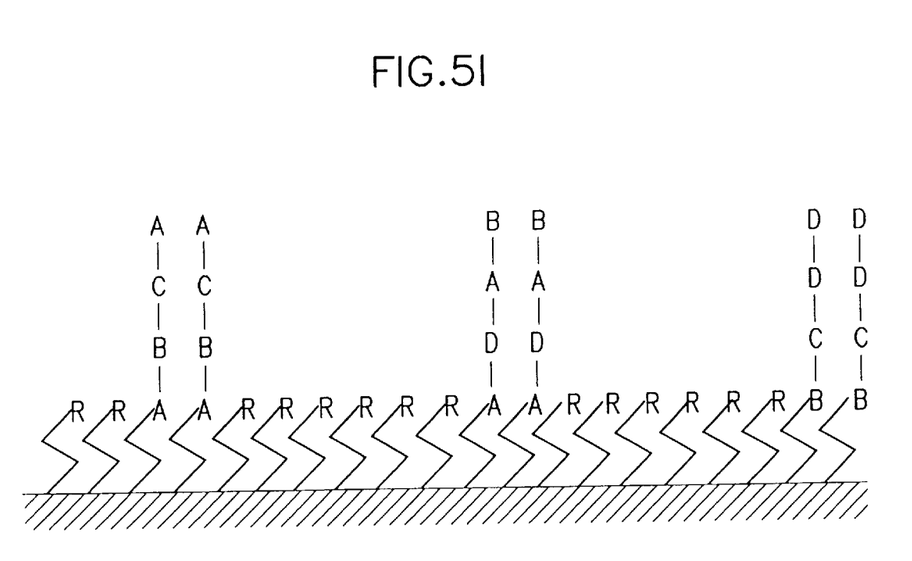

Afterwards, as shown in FIG. 4e, the biomaterial capable of reacting with the activated reaction group is deposited on the substrate by spin coating and the like. Then, coupling reaction occurs in an active pattern region of the spot.

To remove byproducts remaining on a region that does not cause coupling reaction, cleaning and washing processes are performed.

As shown in FIGS. 4f to 4k, the same process steps as FIGS. 4c to 4e are repeatedly performed so that different biomaterials are fixed on a different spot. At this time, the biomaterials are formed of peptide, protein, antibody, DNA, PNA, and enzyme.

FIGS. 5a to 5l show the process for fabricating a DNA chip by synthesizing a oligonucleotide probe of four base length to the round plate type bio chip according to the present invention.

An oligomer probe by synthesization of DNA base is fabricated in such a manner that a spot of the substrate is selectively patterned in the laser addressing method by chip design software of bioinformatics and sequentially synthesized.

The principle of measuring biomaterials using the biochip will now be described.

A sample solution labelled with a fluorescent material or an infrared dye material is reacted with the round plate type DNA chip under hybridization reaction condition and then expression level of DNA can be monitored.

Figure 7:
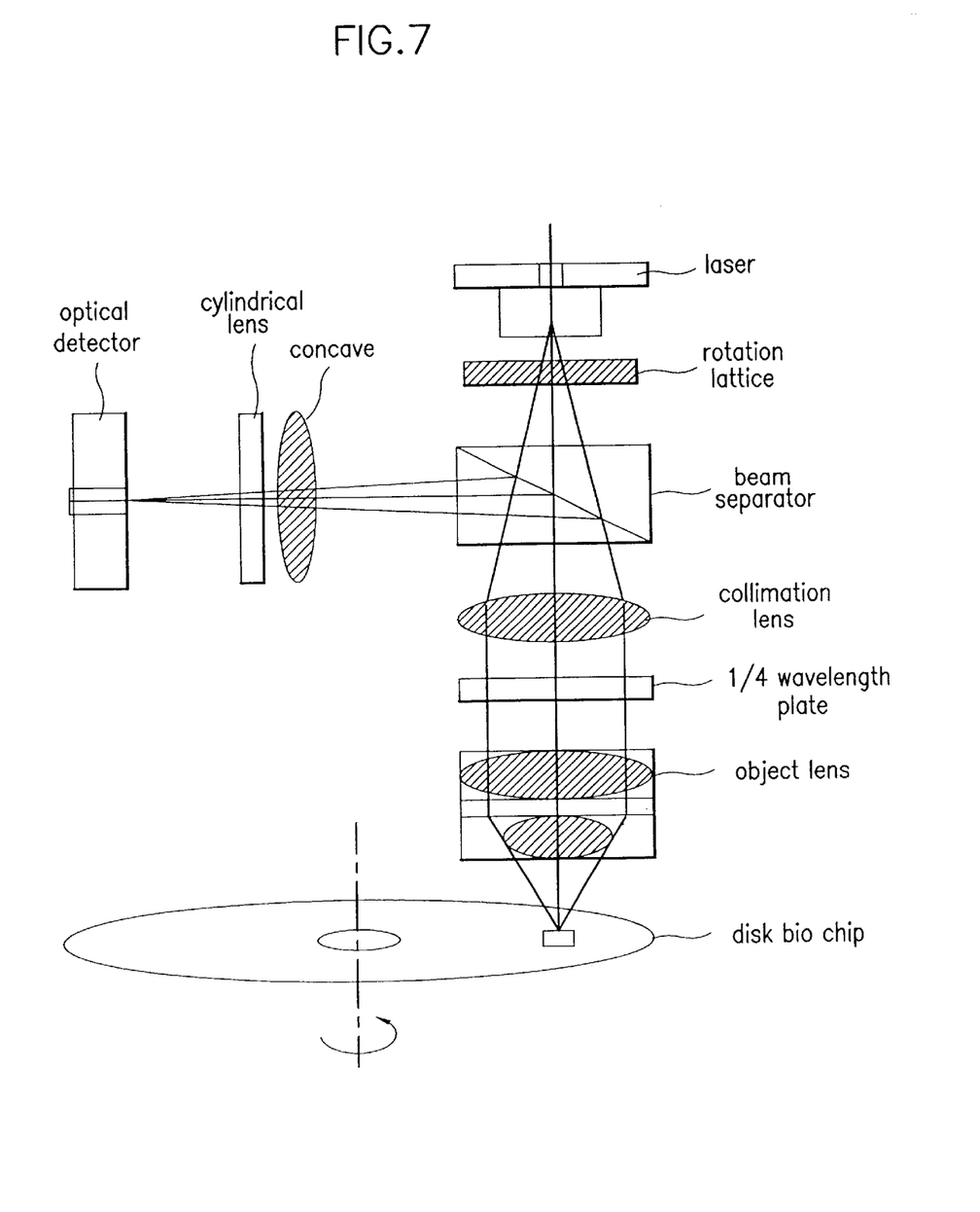
FIG. 7 shows an optical pickup device used to pattern and measure a biomaterial.
Figure 8:
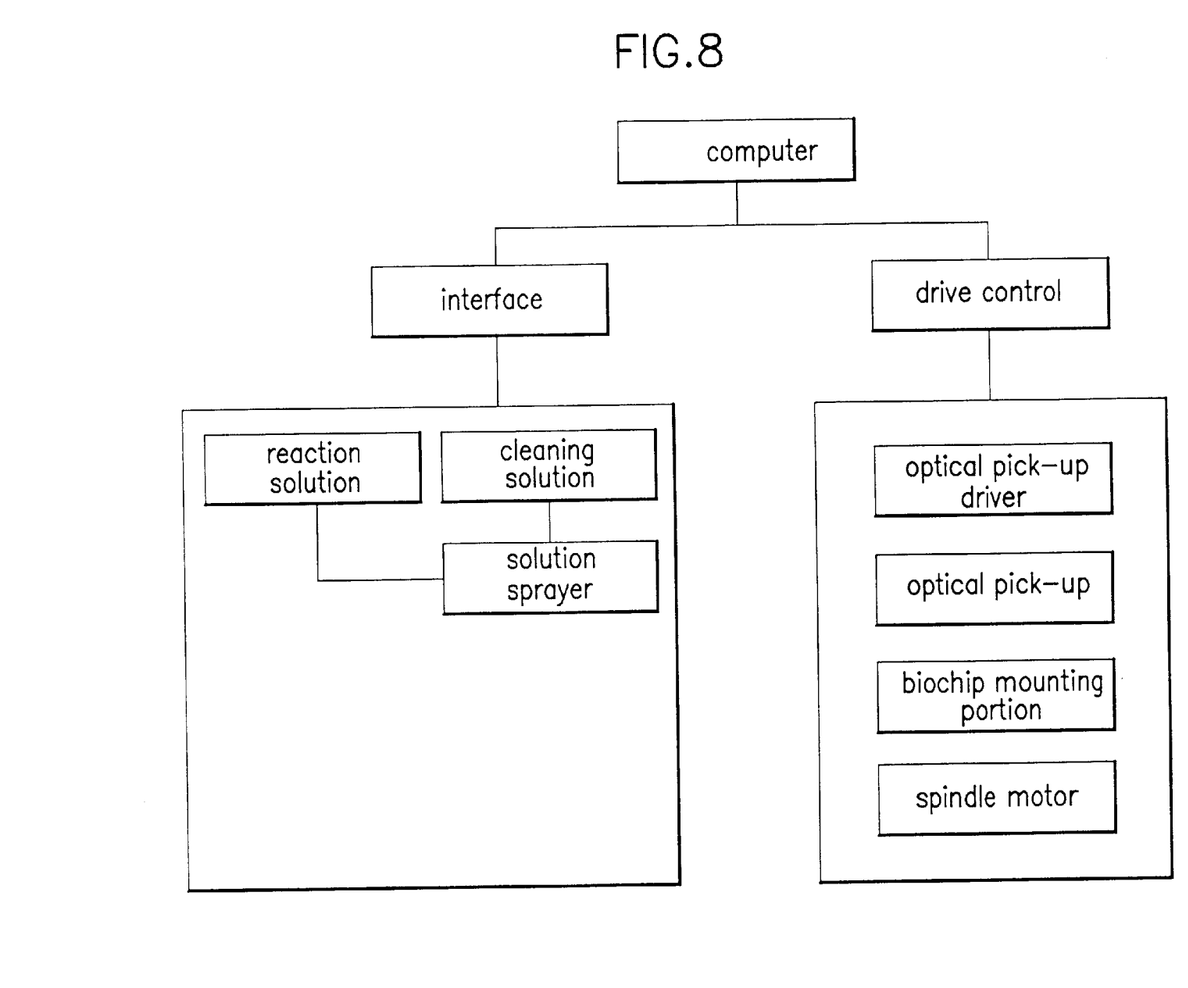
FIG. 8 shows an optical pickup device used in the present invention.

To monitor expression of DNA, as shown in FIGS. 7 and 8, an optical system for recording/reproducing data of a general compact disk is required.

A biomaterial labelled with a fluorescent dye material or an infrared ray dye material is hybridizated with the biochip, and the round plate type biochip is mounted on a biochip mounting portion of a detecting driver. Then, the biochip is rotated by a spindle motor, and fluorescence of the biomaterial fixed on the spot is detected in a laser beam addressing method while the biochip is rotating. Then, signal processing is performed.

The processed signal is analyzed by a computer to confirm reaction of the biomaterial.

In case where a fluorescent dye material is used, a general confocal laser detector can be applied to an optical system of an optical pick-up device.

However, if an infrared dye material is used, an object lens having numerical aperture(NA) of 0.45 and a laser diode having a wavelength of 780 nm are used.

Focusing is performed by astigmatism while tracking control is performed by three-beam focusing to obtain stable characteristic.

If two biomaterials labelled with different dye materials are hybridizated, laser beams having different wavelengths can be used in accordance with kinds of dye materials.

That is, if two dye materials are used, two laser diodes having different wavelengths can be used. At this time, an avalanche photodiode having a greater optical amplification ratio than a photomultiplier tube(PMT) and low cost is used as a detector. In this case, a biochip scanner, i.e., a round plate type biochip drive, capable of substituting for a high priced scanner such as an existing confocal laser scanner can be fabricated.

An apparatus for fabricating a round plate type biochip of the present invention and a drive for detecting a signal will be described with reference to FIG. 8.

Similar to the existing CD-ROM, a drive controller controlled by a computer and an interface are provided. The drive controller includes a servo controller, a data processor and a system processor. The interface acts as a reaction material forming process and a washing process required when fabricating a biochip.

Also, the drive controller controls rotation of the round plate type biochip and driving of the optical pick-up device, and processes a signal read by the optical pick-up device.

That is, the drive controller acts to perform focusing (servo perpendicular to a disk surface) and tracking(servo along a track on a disk surface) required for optical pick-up servo, and at the same time detects fluorescence.

The drive mechanism includes an optical pick-up driver, a round plate biochip loader, and a spindle motor in one united body with a round plate biochip table.

The biochip and the method for patterning and measuring a biomaterial of the same have the following advantages.

First, since a round plate type substrate and a laser addressing method similar to a compact disk is used, it is possible to pattern the biomaterial in a desired spot. Accordingly, different biomaterials can programmably fixed in a limited region and thus it is possible to provide core technology in fabricating a multi-biosensor.

Second, when an oligomer chip is fabricated, a number of masks are not required. Accordingly, mass production of a DNA chip is possible so as to be suitable for various kinds and small quantity of production.

Third, in even case where a protein chip and a peptide chip as well as a DNA chip are fabricated, a round plate type substrate is used, so that in-situ synthesization process can be setup. Accordingly, if a desired biochip design data is provided, the process for fabricating all kinds of biochips can be automatized by a computer programming.

Fourth, the round plate type substrate enhances mixing and washing efficiencies of samples. That is to say, it is possible to enhance reaction efficiency between a portion where the reactor is exposed and the biomaterial.

Fifth, since the optical pick-up device of the existing CDR type is used to measure data of the fabricated round plate type biochip, data processing speed can be improved.

Finally, the infrared dye material is used and the laser diode and the avalanche photodiode are used as a detector, so that a portable scanner(round plate type biochip driver) can be fabricated.

The foregoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. A biochip comprising:

a substrate;

a reflecting layer formed on the entire surface of the substrate;

an active layer formed on the reflecting layer;

a pattern of bound biomaterial formed on a predetermined region of the active layer; and a groove region and a land region, wherein the boundary between the groove region and the land region is of wobble form.

2. The biochip of claim 1, wherein the substrate has a round shape.

3. The biochip of claim 1, wherein the substrate is selected from the group consisting of glass, polycarbonate, polytetrafluoroethylene, polystyrene, silicon oxide, and silicon nitride.

4. The biochip of claim 1, wherein the reflecting layer is of gold or aluminum.

5. The biochip of claim 1, wherein the active layer is of a silicon oxide film formed on the reflecting layer, and a reaction material and a photosensitive material sequentially formed on the silicon oxide film.

6. The biochip of claim 1, wherein the biomaterial is selected from the group consisting of peptides, proteins, antibodies, DNA, PNA and enzymes.

7. A method for patterning a biomaterial on a biochip including a reflecting layer and an active layer on a substrate comprising:

(a) rotating the biochip;

(b) successively irradiating pulse type laser beams to the rotating biochip to activate predetermined regions of the active layer, wherein the laser beams comprise a first beam for sensing a track on the biochip to transmit a position signal for activation and a second beam for activating a spot of the biochip in accordance with the position signal of the first beam;

(c) fixing a pattern of bound biomaterial on the activated predetermined regions; and (d) sequentially repeating steps (b) and (c).

8. The method of claim 7, wherein the biochip is circular and wherein the laser beams are irradiating the biochip while moving from a central portion of the biochip to its outer circumference, or from the outer circumference to the central portion in a straight line.

9. The method of claim 7, further comprising the step of removing residual biomaterials that are not fixed on the predetermined regions after the step (c).

10. A method for using a biochip for measuring a biomaterial, wherein the biochip includes a reflecting layer and an active layer on a subsrate, and wherein the substrate includes a groove region and a land region, wherein the boundary between the groove region and the land region is of wobble form comprising:

reacting a biomaterial labeled with at least one dye material with the biochip;

rotating the biochip with at least one bound biomaterial;

successively irradiating laser beams to the rotating biochip; and detecting and processing light derived from the biochip as a result of reaction of the biomaterial to measure the biomaterial.

11. The method of claim 10, wherein the laser beams have different wavelengths in accordance with dye materials labeled in the biomaterial.

12. The method of claim 10, wherein the dye material is of fluorescent material or infrared ray material.

13. A kit for measuring a biomaterial comprising:

(a) a biochip comprising:
 (i) a substrate, wherein the substrate includes a groove region and a land region, wherein the boundary between the groove region and the land region is of wobble form
 (ii) a reflecting layer formed on the entire surface of the substrate,
 (iii) an active layer formed on the reflecting layer, and
 (iv) a pattern of bound biomaterial formed on a predetermined region of the active layer, and (b) means for labeling a biomaterial with at least one dye material.

14. The kit of claim 13, wherein the substrate has a round shape.

15. The kit of claim 13, wherein the substrate is selected from the group consisting of glass, polycarbonate, polytetrafluoroethylene, polystyrene, silicon oxide, and silicon nitride.

16. The kit of claim 13, wherein the reflecting layer is of gold or aluminum.

17. The kit of claim 13, wherein the active layer is of a silicon oxide film formed on the reflecting layer, and a reaction material and a photosensitive material sequentially formed on the silicon oxide film.

18. The kit of claim 13, wherein the biomaterial is selected from the group consisting of peptides, proteins, antibodies, DNA, PNA and enzymes.

19. The method of claim 7, wherein the substrate includes a groove region and a land region, wherein the boundary between the groove region and the land region is of wobble form.

* * * * *